(12) United States Patent
Nakamura et al.

(10) Patent No.: US 8,563,745 B2
(45) Date of Patent: Oct. 22, 2013

(54) PROCESS FOR PRODUCING ISOTHIAZOLE DERIVATIVE

(75) Inventors: Takayuki Nakamura, Fuji (JP); Hironobu Kumagai, Fuji (JP); Mahito Ogawa, Fuji (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/318,323

(22) PCT Filed: Apr. 30, 2010

(86) PCT No.: PCT/JP2010/057981
§ 371 (c)(1),
(2), (4) Date: Oct. 31, 2011

(87) PCT Pub. No.: WO2010/126170
PCT Pub. Date: Nov. 4, 2010

(65) Prior Publication Data
US 2012/0046473 A1     Feb. 23, 2012

(30) Foreign Application Priority Data

May 1, 2009    (JP) .................................. 2009-111840
May 1, 2009    (JP) .................................. 2009-111841

(51) Int. Cl.
*C07D 275/03*    (2006.01)

(52) U.S. Cl.
USPC ........................................................ 548/214

(58) Field of Classification Search
USPC ........................................................ 548/214
See application file for complete search history.

(56) References Cited

U.S. PATENT DOCUMENTS 5,240,951 A    8/1993    Shimotori et al.

FOREIGN PATENT DOCUMENTS

| DE | 2 231 097 A | 1/1974 |
|---|---|---|
| DE | 2 231 098 A | 1/1974 |
| JP | 5-59024 A | 3/1993 |
| JP | 2009-500302 A | 1/2009 |

OTHER PUBLICATIONS

S. Nakagawa, et al., "Synthesis of Sulfer-Containing Heterocycles Using Thionyl Chloride or Sulfur Chlorides", Tetrahedron Letters, 1970, No. 42, pp. 3719-3722.

*Primary Examiner* — Laura L. Stockton
(74) *Attorney, Agent, or Firm* — Arent Fox LLP

(57) ABSTRACT

A process for producing 3,4-dichloro-5-cyanoisothiazole represented by a general formula (3):

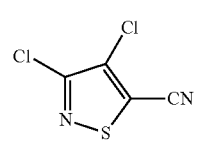

(3)

the process comprising:
reacting a nitrile compound represented by a general formula (1):

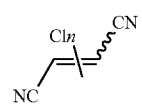

(1)

(wherein "n" denotes an integer of 0 to 2), with sulfur chloride represented by a general formula (2):

$S_mCl_2$    (2)

(wherein "m" represents an integer of 1 to 2), or a mixture thereof in an aprotic polar solvent. There is provided a process for producing 3,4-dichloro-5-cyanoisothiazole, which is capable of suppressing by-production of a waste, without using a raw material having a strong toxicity; and is capable of providing a product having a higher purity in a high yield and efficiency in an industrial scale, in a simple manner.

11 Claims, No Drawings

US 8,563,745 B2

PROCESS FOR PRODUCING ISOTHIAZOLE DERIVATIVE

CROSS-REFERENCE TO RELATED APPLICATION

This application is a National Stage entry of International Application No. PCT/JP2010/057981, filed Apr. 30, 2010, which claims priority to Japanese Patent Application Nos. 2009-111840 filed on May 1, 2009, and 2009-111841 filed on May 1, 2009 filed.

TECHNICAL FIELD

The present invention relates to a process for producing an isothiazole derivative. The isothiazole derivative is useful, for example, as an intermediate for synthesizing various organic compounds (e.g., biologically active organic compounds such as pharmaceutical compounds and agricultural chemicals, functional coloring matters, and electronic materials), because of the presence of the isothiazole structure thereof.

BACKGROUND ART

Isothiazole derivatives are widely known as intermediates to be used for pharmaceuticals and a agricultural chemicals, intermediates for functional coloring matters, and electronic materials. Various studies have heretofore been made processes for producing isothiazole derivatives (please refer to Non-Patent Document 1 and Non-Patent Document 2). Among these production processes, 3,4-dichloro-5-cyanoisothiazole, which is can easily be subjected to a functional group conversion thereof, has been used as an intermediate for pharmaceutical compounds and agricultural chemicals. In fact, this compound has been used as an important intermediate for a agricultural chemical, as disclosed in JP-A (Japanese Unexamined Patent Publication; KOKAI) No. 5-59024, and Japanese Patent No. 4,088,036. However, the production process disclosed in the above-mentioned Non-Patent Document 1 can only provide a low yield of the product. Further, the production process disclosed in the above-mentioned Non-Patent Document 2 cannot produce 3,4-dichloro-5-cyanoisothiazole having a specific structure, which is useful as an important intermediate for an agricultural chemical.

A process using carbon disulfide ($CS_2$), sodium cyanide (NaCN) and chlorine ($Cl_2$) has heretofore been known as a process for producing 3,4-dichloro-5-cyanoisothiazole (please refer to Patent Document 1). However, this process has such drawback that a specially flammable material such as $CS_2$ is used as a raw material to be used therein, and also has another drawback that a toxic material such as NaCN is used therein. In addition, this process exhibits a low yield and is an ineffective process, and also has a drawback that a large amount of wastes are produced as by-products. Examples of the wastes may include by-produced sulfur. In this process, chlorine is introduced into a reactor containing therein dimethylformamide (DMF) as a solvent under heating, and therefore, runaway of a reaction can occur. Further, a 3,4-dichloro-5-cyanoisothiazole derivative which has been produced by this process contains a large amount of tar components, the product must be purified in a purification step such as distillation, and accordingly this process is not an industrially preferred production process. As another production process, a process using trichloroacetonitrile and sulfur is known (please refer to Patent Document 2). However, this process is not an industrially preferred production process, because it exhibits a low yield and is ineffective, and also requires a high reaction temperature. Further, a process using dichlorofumaronitrile and sulfur is also known (please refer to Patent Document 3). However, this process is not an industrially preferred production process, because it only provides a low yield and is ineffective, and also because a high reaction temperature is required therein.

PRIOR ART DOCUMENTS

Patent Documents

[Patent Document 1] U.S. Pat. No. 3,341,547 A
[Patent Document 2] DE 2231097 A (DT 2231097)
[Patent Document 3] DE 2231098 A (DT 2231098)

Non-Patent Documents

[Non-Patent Document 1] Tetrahedron Lett. 42, (1970) 3719-3722
[Non-Patent Document 2] Chem. Commun. 2002, 1872-1873

DISCLOSURE OF THE INVENTION

Problems to be Solved by the Invention

An object of the present invention is to provide a process for producing 3,4-dichloro-5-cyanoisothiazole, which can solve the above-mentioned one or more drawbacks encountered in the prior art.

Another object of the present invention is to provide a process for producing 3,4-dichloro-5-cyanoisothiazole, which can suppress by-production of a waste, without substantially using a raw material having a drawback in the use thereof (for example, a raw material having a strong toxicity).

A further object of the present invention is to provide a process for producing 3,4-dichloro-5-cyanoisothiazole, which can suppress the production of a tar component, and can provide a product having a higher purity in a high yield and efficiency (for example, in an industrial scale, in a simple manner).

Means for Solving the Problems

As a result of earnest study on a process for producing 3,4-dichloro-5-cyanoisothiazole in view of the above circumstances, the present inventors have found that the above-mentioned object can unexpectedly be solved, by reacting sulfur chloride with fumaronitrile, maleonitrile, or a chlorine-substituted compound thereof, or a mixture of these compounds. The present inventors have completed based on the above discovery.

Effects of the Invention

The present invention provides a novel industrially applicable process for producing 3,4-dichloro-5-cyanoisothiazole. By use of the process according to the present invention, 3,4-dichloro-5-cyanoisothiazole can be produced in a simple operation by using, as a raw material, available fumaronitrile or maleonitrile, or a chlorine-substituted compound thereof or a mixture of these compounds. As a raw material such as fumaronitrile or maleonitrile or chlorine-substituted compounds thereof, it is also possible to use fumaronitrile or maleonitrile or a chlorine-substituted compound thereof or a mixture of these compounds, which have been produced by the chlorination of succinonitrile, whereby 3,4-dichloro-5-cyanoisothiazole can be produced in a simple operation.

Further, in the process according to the present invention, it is possible to produce 3,4-dichloro-5-cyanoisothiazole, which contains no tar component and has a higher purity, with a high yield and efficiency, in an industrial scale and in a simple manner without using a raw material having a strong toxicity, while suppressing the by-production of a waste thereby. Accordingly, the process according to the present invention is environmentally friendly and also has a high industrial utility value.

MODE FOR CARRYING OUT THE INVENTION

The present invention will be disclosed in detail below.

According to the present invention, the above-mentioned object can be solved by providing inventions according to the following embodiments (1) to (19).

[1] A process for producing 3,4-dichloro-5-cyanoisothiazole represented by a general formula (3):

[Chemical Formula 3]

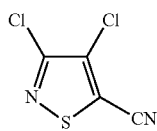

(3)

the process comprising:
reacting a nitrile compound represented by a general formula (1):

[Chemical Formula 1]

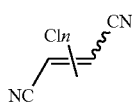

(1)

(wherein "n" denotes an integer of 0 to 2),
with sulfur chloride represented by a general formula (2):

[Chemical Formula 2]

$S_mCl_2$ (2)

(wherein "m" represents an integer of 1 to 2),
or a mixture thereof in an aprotic polar solvent.

[2] A process for producing 3,4-dichloro-5-cyanoisothiazole according to [1], wherein the nitrile compound is a nitrile compound of the general formula (1) wherein "n" is 0.

[3] A process for producing 3,4-dichloro-5-cyanoisothiazole according to [1], wherein the nitrile compound is a nitrile compound represented by the general formula (1) wherein "n" is 1.

[4] A process for producing 3,4-dichloro-5-cyanoisothiazole according to [1], wherein the nitrile compound is a nitrile compound represented by the general formula (1) wherein "n" is 2.

[5] A process for producing 3,4-dichloro-5-cyanoisothiazole according to [1], wherein the nitrile compound is a mixture of a nitrile compound represented by the general formula (1) wherein "n" is 0 to 2.

[6] A process for producing 3,4-dichloro-5-cyanoisothiazole according to any one of [1] to [5], wherein the aprotic polar solvent is an amide-based aprotic polar solvent or a carbonate ester-based aprotic polar solvent.

[7] A process for producing 3,4-dichloro-5-cyanoisothiazole according to any one of [1] to [6], wherein the aprotic polar solvent is dimethylformamide, dimethylacetamide, diethylacetamide, N-methylpyrrolidone, tetramethylurea, hexamethylphosphoric triamide, ethylene carbonate or propylene carbonate, or a mixed solvent thereof.

[8] A process for producing 3,4-dichloro-5-cyanoisothiazole according to any one of [1] to [6], wherein the aprotic polar solvent is dimethylformamide, dimethylacetamide, diethylacetamide, N-methylpyrrolidone, tetramethylurea or a mixed solvent thereof.

[9] A process for producing 3,4-dichloro-5-cyanoisothiazole according to any one of [1] to [8], wherein the sulfur chloride represented by a general formula (2) wherein "m" is 1 or 2, or a mixture thereof is prepared in a reaction system.

[10] A process for producing 3,4-dichloro-5-cyanoisothiazole according to any one of [1] to [9], wherein sulfur chloride represented by a general formula (2) is sulfur monochloride represented by a general formula wherein "m" is 2.

[11] A process for producing 3,4-dichloro-5-cyanoisothiazole according to [1] or any one of [3] to [10], wherein the nitrile compound represented by a general formula (1):

[Chemical Formula 4]

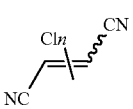

(1)

(wherein "n" is 1 or 2), is produced by chlorination of succinonitrile represented by a general formula (4):

[Chemical Formula 5]

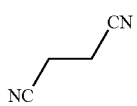

(4)

[12] A process for producing 3,4-dichloro-5-cyanoisothiazole represented by the general formula (3):

[Chemical Formula 9]

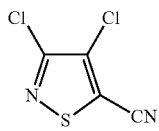

(3)

the process comprising: reacting succinonitrile represented by the general formula (4):

[Chemical Formula 6]

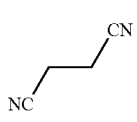

(4)

with chlorine represented by the general formula (5):

[Chemical Formula 7]

Cl₂                    (5)

and reacting the reaction product, with sulfur chloride represented by the general formula (2):

[Chemical Formula 8]

S$_m$Cl₂              (2)

wherein m represents an integer of 1 to 2, or a mixture thereof, in an aprotic polar solvent.

[13] A process for producing 3,4-dichloro-5-cyanoisothiazole according to [12], wherein the aprotic polar solvent is an amide-based aprotic polar solvent or a carbonate ester-based aprotic polar solvent.

[14] A process for producing 3,4-dichloro-5-cyanoisothiazole according to [12], wherein the aprotic polar solvent is an amide-based aprotic polar solvent.

[15] A process for producing 3,4-dichloro-5-cyanoisothiazole according to [12], wherein the aprotic polar solvent is dimethylformamide, dimethylacetamide, diethylacetamide, N-methylpyrrolidone, tetramethylurea, hexamethylphosphoric triamide, ethylene carbonate or propylene carbonate, or a mixed solvent thereof.

[16] A process for producing 3,4-dichloro-5-cyanoisothiazole according to [12], wherein the aprotic polar solvent is dimethylformamide, dimethylacetamide, diethylacetamide, N-methylpyrrolidone, tetramethylurea or a mixed solvent thereof.

[17] A process for producing 3,4-dichloro-5-cyanoisothiazole according to any one of [12] to [16], wherein the reaction of succinonitrile represented by the general formula (4) with chlorine represented by the general formula (5) is carried out in the absence of a solvent.

[18] A process for producing 3,4-dichloro-5-cyanoisothiazole according to any one of [12] to [17], wherein sulfur chloride of the general formula (2) in which m is 1 or 2, or a mixture thereof is prepared in a reaction system.

[19] A process for producing 3,4-dichloro-5-cyanoisothiazole according to any one of [12] to [18], wherein sulfur chloride represented by the general formula (2) is sulfur monochloride represented by the formula in which m is 2.

Hereinbelow, the present invention will be described in more detail.

(Process for Producing Isothiazole Derivative)

The process according to the present invention is a process for producing 3,4-dichloro-5-cyanoisothiazole represented by a general formula (3), characterized in that the process includes: reacting a nitrile compound represented by a general formula (1) with a sulfur chloride represented by a general formula (2), in an aprotic polar solvent.

(Raw Material Compound)

At first, the above-mentioned raw material compound represented by a general formula (1) or the like to be used as the raw material for the process according to the present invention will be described.

(Nitrile Compound)

In the general formula (1), "n" denotes an integer of 0 to 2.

Specific examples of the nitrile compound represented by the general formula (1), which can be used in this reaction, may include: fumaronitrile, maleonitrile, monochloro fumaronitrile, dichloro fumaronitrile, monochloro maleonitrile, dichloro maleonitrile, or a mixture thereof.

All of these nitrile compounds represented by the general formula (1) are known compounds.

Among the above compounds represented by the general formula (1), a nitrile compound in which "n" is 1 or 2 can be produced by the chlorination of succinonitrile represented by the formula (4). The succinonitrile represented by the general formula (4) is now commercially available, industrially, at a relatively low cost, and is also a preferred known compound as an industrial raw material, in view of handling and toxicity thereof. The chlorination of the succinonitrile represented by the general formula (4) may be either thermal chlorination or photochlorination. The chlorination of the succinonitrile can also be carried out by using the photochlorination in accordance with that disclosed in U.S. Pat. No. 2,443,494.

(Chlorination of Succinonitrile)

The chlorination reaction of the succinonitrile can be carried out, for example, by introducing, as a chlorinating agent, chlorine represented by the general formula (5)

[Chemical Formula 10]

Cl₂              (5)

into a reaction system by blowing, to thereby use it as a reaction reagent. The amount of chlorine represented by the general formula (5) to be used in this reaction may preferably be 0.1 equivalent or more, with respect to the raw material compound. The amount of chlorine to be used for such a purpose may preferably be generally in the range of 0.1 to 10.0 equivalents, and more preferably 0.1 to 3.0 equivalents, based on the succinonitrile represented by the general formula (4).

(Chlorinating Agent)

The chlorinating agent to be used is not limited to the above-mentioned chlorine, and the chlorination can also be carried out by using another chlorinating agent known in the art. Examples of the "other known chlorinating agent" may include: N-chlorosuccinimide, phosphorus pentachloride, phosphorus trichloride, phosphorus oxychloride, sulfuryl chloride, thionyl chloride, hydrogen chloride and the like.

(Solvent)

This reaction may preferably be carried out in the absence of a solvent. However, as long as the present reaction and the reaction of the subsequent step are not inhibited, it is also possible to carry out the reaction in the presence of an appropriate solvent. The solvent to be usable in this reaction may include any solvent, as long as it functions as a liquid solvent at a reaction temperature, and it does not inhibit this reaction and the reaction in the subsequent step. Specific examples of the solvent may include: for example, a hydrocarbon solvent having 6 to 40 carbon atoms, such as by hexane, heptane, octane, nonane, decane, undecane, dodecane, tridecane, tetraecane, pentadecane, heptadecane, octadecane, nonadecane, eicosane, pentacosane, triacontane, tetracontane and liquid paraffin, and a mixture thereof. The amount of the solvent to be used may preferably be generally in the range of 10.0 L (liter) or less, and more preferably 0.01 to 2.0 L, based on 1 mol of the raw material compound represented by the general formula (4).

(Reaction Temperature)

The reaction temperature of this reaction may be generally in the range of 60° C. to 200° C., and preferably 90° C. to 160° C.

(Reaction Time)

The reaction time of this reaction is not particularly limited. In view of the suppression of a by-products or the like, the reaction time may generally be 0.5 hour to 48 hours, and may preferably be 8 hours to 36 hours.

(Process for Using Nitrile Compound)

In the process according to the present invention, any one of nitrile compounds represented by the general formula (1) in which "n" is 0 to 2 can be used alone as the raw material. In a case where the above-mentioned step is carried out in the absence of a solvent, it is possible that the resultant reaction mixture (solution) obtained by the above step as a crude product (in general, the crude product is a mixture of a plurality of nitrile compounds represented by the general formula (1) in which "n" is 0 to 2) is reacted with sulfur dichloride represented by the general formula (2) in an aprotic polar solvent, as it is (i.e., without being subjected to a specific purification step), to thereby produce an intended product of 3,4-dichloro-5-cyanoisothiazole.

(Sulfur Chloride)

Subsequently, sulfur chloride represented by a general formula (2) will be described.

In the above-mentioned general formula (2), "m" represents an integer of 1 to 2.

Therefore, specific examples the sulfur chloride represented by a general formula (2), which is usable in this reaction, may include sulfur dichloride in which "m" is 1, or sulfur monochloride in which "m" is 2. These compounds can also be synthesized from sulfur and chlorine in the system or outside the system. In view of the availability, ease of handling, reactivity and the like, sulfur monochloride may preferably be used.

These sulfur chloride represented by a general formula (2) are known compounds.

(Amount of Sulfur Chloride to be Used)

Regarding the molar ratio of the sulfur dichloride to be used represented by a general formula (2) in this reaction, the reaction can proceed in any molar ratio with respect to that of the raw material compound represented by the general formula (1). The amount of the sulfur chloride represented by a general formula (2) may generally be in the range of 1.0 to 10.0 mol, and preferably 1.0 to 4.0 mol, based on 1 mol of the nitrile compound represented by the general formula (1) (i.e., raw material compound).

The amount of sulfur monochloride to be used may preferably be an equivalent or more, with respect to the raw material compound. Generally, the amount thereof to be used may preferably be in the range of 1.0 to 10.0 equivalents, and more preferably 1.0 to 4.0 equivalents, based on 1 mol of the raw material compound represented by the general formula (1).

(Solvent)

The reaction can be carried out by using an aprotic polar solvents which is usable in this reaction. Specific examples thereof may include: e.g., dimethylformamide, dimethylacetamide, N-methylpyrrolidone, tetramethylurea, hexamethylphosphoric triamide, ethylene carbonate and propylene carbonate. In view of the reactivity, and the simplicity of a post-treatment to be used therefor, N,N-dimethylformamide and N-methylpyrrolidone may preferably be used. The solvents can be used alone, or used as a mixed solvent in an arbitrary mixing ratio.

(Aprotic Solvent)

Examples of the aprotic solvent may include: diethylether, tetrahydrofuran, N,N-dimethylformamide, N,N-diethylformamide, N,N-dimethylacetamide, N,N-diethylacetamide, N-methylpyrrolidone, tetramethylurea, hexamethylphosphoric triamide, pyridine, benzonitrile, acetonitrile, propylene carbonate, dimethyl sulfoxide, nitromethane and chloroform. However, the aprotic solvent to be used in the present invention are not limited to these specific examples.

(Acceptor Number)

The aprotic solvent as used herein refers to a solvent having an acceptor number of 24.0 or less.

The solvent used in this reaction may preferably be an aprotic solvent having an acceptor number (AN) of 24.0 or less, more preferably an aprotic solvent having an acceptor number (AN) of 20.0 or less, and still more preferably an aprotic solvent having an acceptor number (AN) of 17.0 or less.

The acceptor number (AN) is disclosed in V. Gutmann (translated by Ohtaki and Okada) "Donor and Acceptor, Japan Scientific Societies Press (Gakkai Shuppan Center), 1983; or Christian Reichardt [Solvents and Solvent Effects in Organic Chemistry, 2nd edition, VCH (RFA), 1990, pp.23-24] and the like.

Herein the acceptor number (AN) is an indicator of acceptor property, for example, proposed by Mayer-Gutmann. When the $^{31}$P-NMR chemical shift value of $(C_2F_5)3PO$ dissolved in n-hexane is set to 0, and the $^{31}$P-NMR chemical shift value of a $(C_2F_5)3PO\cdot SbCl_5$ complex in 1,2-dichloroethane is set to 100, the $^{31}$P-NMR chemical shift value of $(C_2F_5)3PO$ dissolved in a certain pure solvent is regarded as "AN". That is, $AN=100\delta$ (solvent)/$[\delta((C_2F_5)3PO\cdot SbCl_5$ in 1,2-dichloroethane$)-\delta((C_2F_5)3PO)$ dissolved in n-hexane].

(Dielectric Constant)

The polar solvent as used herein refers to a solvent having a dielectric constant of 5 or more. Here, the dielectric constant is regarded as a value disclosed in "KagakuBinran Kisohen (Handbook of Chemistry: Fundamentals Section)", edited by The Chemical Society of Japan, Revised 5th edition, pp. I-770-777, MARUZEN Co., Ltd., 2004.

(Amount of Solvent)

The amount of the solvent may preferably be an amount such that it enables sufficient stirring in a reaction system. For example, the amount of the solvent can be in the range of 0.01 to 10 L, and preferably 0.1 to 1.0 L, and more preferably 0.1 to 0.5 L, based on 1 mol of the raw material compound represented by the general formula (1).

(Reaction Temperature)

The reaction temperature of this reaction can be in the range of 70° C. to a reflux temperature of the solvent, and may preferably be 90° C. to 120° C.

(Reaction Time)

The reaction time of this reaction is not particularly limited. In view of the suppression of by-products, the reaction time may preferably be 1 hour to 20 hours.

According to this reaction, 3,4-dichloro-5-cyanoisothiazole represented by the general formula (3) can be produced in a high yield under a mild condition without using a specially designed reactor. The thus obtained 3,4-dichloro-5-cyanoisothiazole represented by the general formula (3) is a compound, which is useful as an intermediate raw material for pharmaceutical compounds, agricultural chemical compounds and the like.

(Yield)

In the present invention, the yield of the intended product may preferably be 70% or more, more preferably 75 to 95%, and still more preferably 80 to 95% (particularly preferably 83 to 95%).

This yield can be calculated from the number of mols of the obtained intended product 3,4-dichloro-5-cyanoisothiazole with respect to the number of mols of the nitrile compound represented by the general formula (1), as the raw material.

That is, the yield in the present invention can be represented by the following equation.

Yield (%)=100×(number of mols of the obtained intended product)/(number of mols of the raw material represented by the general formula (1)))

In the Examples 1 to 8 appearing hereinafter, 1 (one) mol of the intended product of 3,4-dichloro-5-cyanoisothiazole can be theoretically produced from 1 mol of the nitrile compound represented by the general formula (1), as the raw material. Therefore, an actual yield can be calculated from this theoretical value.

On the other hand, in the Comparative Example 1 appearing hereinafter, 1 mol of the intended product of 3,4-dichloro-5-cyanoisothiazole can be theoretically produced from 2 mol of carbon disulfide as the raw material. Accordingly, the yield in Comparative Example 1 or the like can be expressed by such a percentage of a "theoretical yield" (based on 2 mol of carbon disulfide).

EXAMPLES

The production process according to the present invention compound will be descried in more detail by way of Examples, but the present invention is not limited by these Examples.

Example 1

Production of 3,4-dichloro-5-cyanoisothiazole

In a 300 ml four-necked flask equipped with a stirrer, a reflux condenser, a thermometer and a dropping funnel, 7.80 g (0.100 mol) of fumaronitrile and 50 ml (0.520 mol) of N-methylpyrrolidone were charged, and 32 ml (0.400 mol) of sulfur monochloride was added dropwise at 20 to 25° C. under stirring. The temperature was raised to 100° C., and thereafter, the resultant reaction mixture was stirred for 6 hours. The reaction solution was cooled to 25° C. and water was added dropwise thereto, while paying attention to the temperature, and then the precipitated sulfur was removed by filtration.

Then, the reaction product was extracted with toluene to thereby obtain the product as a pale brown toluene solution containing little amount of tar component. This toluene solution was analyzed by a HPLC absolute calibration curve method. As a result, it was found that the resultant yield of 3,4-dichloro-5-cyanoisothiazole was 92%. The structure of the thus obtained 3,4-dichloro-5-cyanoisothiazole as the toluene solution was confirmed by using spectrum measurement.

$^{13}$C-NMR 75 MHz (CHCl$_3$-d$_1$, δ): 108.2, 130.9, 131.0, 149.8. GC-MS(m/z): 178[M−1]$^+$, 180[M+1]$^+$.

Example 2

Production of 3,4-dichloro-5-cyanoisothiazole

In a 300 ml four-necked flask equipped with a stirrer, a reflux condenser, a thermometer and a dropping funnel, 8.98 g (0.115 mol) of fumaronitrile and 76.5 ml (0.990 mol) of N,N-dimethylformamide were charged, and 36.8 ml (0.460 mol) of sulfur monochloride was added dropwise at 20 to 25° C. under stirring. The temperature was raised to 100° C., and thereafter, the resultant reaction mixture was stirred for 6 hours. The reaction solution was cooled to 25° C. and water was added dropwise thereto, while paying attention to the temperature, and then the precipitated sulfur was removed by filtration.

Then, the reaction product was extracted with toluene to thereby obtain the product as a pale brown toluene solution containing little amount of tar component. This toluene solution was analyzed by a HPLC absolute calibration curve method. As a result, it was found that the resultant yield of 3,4-dichloro-5-cyanoisothiazole was 71%.

Example 3

Production of 3,4-dichloro-5-cyanoisothiazole

In a 25 ml recovery (or egg plant flask, 1.47 g (10

In a 25 ml recovery (or egg plant flask), 1.47 g (10 mmol) of dichloro fumaronitrile and 2.5 ml of N,N-dimethylformamide were charged and 2.0 g (15 mmol) of sulfur monochloride was added dropwise at 20 to 25° C. under stirring. The temperature was raised to 100° C., and thereafter, the resultant reaction mixture was stirred for 6 hours. The reaction rate observed with GC (gas chromatography) analysis was 100%. The reaction solution was cooled to 25° C. and water was added dropwise thereto, while paying attention to the temperature, and then the precipitated sulfur was removed by filtration.

Then, the reaction product was extracted with toluene to thereby obtain the product as a pale brown toluene solution containing little amount of tar component. This toluene solution was analyzed by a HPLC absolute calibration curve method. As a result, it was found that the resultant yield of 3,4-dichloro-5-cyanoisothiazole was 79%.

Example 4

Production of 3,4-dichloro-5-cyanoisothiazole

In a 25 ml recovery flask, 1.12 g (10 mmol) of monochloro fumaronitrile and 2.5 ml of N,N-dimethylformamide were charged and 2.0 g (15 mmol) of sulfur monochloride was added dropwise at 20 to 25° C. under stirring. The temperature was raised to 100° C., and thereafter, the resultant reaction mixture was stirred for 3 hours. The reaction rate observed with GC analysis was 97.5%. The reaction solution was cooled to 25° C. and water was added dropwise thereto, while paying attention to the temperature, and then the precipitated sulfur was removed by filtration.

Then, the reaction product was extracted with toluene to thereby obtain the product as a pale brown toluene solution containing little amount of tar component. This toluene solution was analyzed by a HPLC absolute calibration curve method. As a result, it was found that the resultant yield of 3,4-dichloro-5-cyanoisothiazole was 76%.

Example 5

Production of 3,4-dichloro-5-cyanoisothiazole

In a 25 ml recovery flask, 1.12 g (10 mmol) of monochloro maleonitrile and 2.5 ml of N,N-dimethylformamide were charged and 2.0 g (15 mmol) of sulfur monochloride was added dropwise at 20 to 50° C. under stirring. The temperature was raised to 100° C., and thereafter, the resultant reaction mixture was stirred for 3 hours. The reaction rate observed with GC analysis was 95.5%. The reaction solution was cooled to 25° C. and water was added dropwise thereto, while paying attention to the temperature, and then the precipitated sulfur was removed by filtration.

Then, the reaction product was extracted with toluene to thereby obtain the product as a pale brown toluene solution containing little amount of tar component. This toluene solution was analyzed by a HPLC absolute calibration curve method. As a result, it was found that the resultant yield of 3,4-dichloro-5-cyanoisothiazole was 80%.

Example 6

Production of 3,4-dichloro-5-cyanoisothiazole

In a 25 ml recovery flask, 57 mg (0.39 mmol) of dichloromaleonitrile and 120 mg of N,N-dimethylformamide were charged and 159 mg (1.18 mmol) of sulfur monochloride was added dropwise at 20 to 25° C. under stirring. The temperature was raised to 100° C., and thereafter, the resultant reaction mixture was stirred for 6 hours. The reaction solution was cooled to 25° C. and water was added dropwise thereto, while paying attention to the temperature, and then the precipitated sulfur was removed by filtration.

Then, the reaction product was extracted with toluene to thereby obtain the product as a pale brown toluene solution containing little amount of tar component.

As a result of GC analysis, it was found that the resultant yield of 3,4-dichloro-5-cyanoisothiazole was 92% in terms of the GC area percentage.

Example 7

Production of 3,4-dichloro-5-cyanoisothiazole

In a 100 ml four-necked flask equipped with a stirrer, a reflux condenser and a thermometer, 60.2 g (0.75 mol) of succinonitrile was charged. The temperature was raised to 120° C., and then, 149.2 g (2.10 mol) of chlorine was introduced thereinto by blowing for 16 hours under stirring. The temperature of the reaction mixture was cooled to room temperature, the reaction solution was subjected to GC analysis. As a result, it was found that the nitrile compound represented by the general formula (1) (wherein "n" denotes an integer of 0 to 2) is a mixture of dichloro fumaronitrile, monochloro fumaronitrile, monochloromaleonitrile, dichloromaleonitrile, maleonitrile and fumaronitrile, and the composition ratio thereof was 9.0:5.9:5.3:5.1:1.5:1.0.

This mixture was transferred to a 1 L four-necked flask equipped with a stirrer, a reflux condenser, a thermometer and a dropping funnel, and 180 ml of N,N-dimethylformamide was charged thereto, and then 90 ml (1.5 mol) of sulfur monochloride was added at 20 to 25° C. under stirring. The temperature was raised to 100° C., and then the mixture was stirred for 9 hours. The reaction solution was cooled to 25° C. and water was added dropwise while paying attention to the temperature, and then the reaction product was extracted with toluene to thereby obtain the product as a brown toluene solution containing little amount of tar component.

This toluene solution was analyzed by a HPLC absolute calibration curve method. As a result, it was found that the yield of 3,4-dichloro-5-cyanoisothiazole was 84%, with respect to the theoretical amount thereof calculated from the amount of the succinonitrile.

Example 8

Production of 3,4-dichloro-5-cyanoisothiazole

In a 50 ml four-necked flask equipped with a stirrer bar, a reflux condenser and a thermometer, 22.0 g (0.27 mol) of succinonitrile was charged thereto, and the resultant mixture was stirred by using a magnetic stirrer while the temperature was being raised to 120° C. While sufficiently paying attention, 65.0 g (0.92 mol) of chlorine was introduced into the flask by blowing for 11 hours. The temperature was cooled to room temperature, then the resultant mixture of dichloro fumaronitrile, monochloro fumaronitrile, monochloromaleonitrile, dichloromaleonitrile, maleonitrile and fumaronitrile as the thus obtained nitrile compound represented by the general formula (1) (wherein "n" denotes an integer of 0 to 2) was transferred to a 1 L four-necked flask equipped with a stirrer, a reflux condenser, a thermometer and a dropping funnel. Under stirring, 140 ml (1.42 mol) of N-methylpyrrolidone and 87.8 ml (1.1 mol) of sulfur monochloride were added thereto at 20 to 25 C 20 to 25° C.

After the temperature was raised to 100° C., the mixture was stirred for 6 hours. The reaction solution was left standing to cool to 25° C., and then the solution was poured into ice water, and the resultant precipitated sulfur was removed therefrom by filtration. Then, the reaction product was extracted with toluene to thereby obtain the product as a brown toluene solution containing little amount of tar component. This toluene solution was analyzed by a HPLC absolute calibration curve method. As a result, it was found that the yield of 3,4-dichloro-5-cyanoisothiazole was 84% with respect to the theoretical amount calculated from the amount of the succinonitrile.

The by-produced sulfur was obtained in a wt. amount which was 0.27 times that of the intended product.

Comparative Example 1

Synthesis of 3,4-dichloro-5-cyanoisothiazole: Process Disclosed in Patent Document 1

In a nitrogen-charged 500 ml four-necked flask equipped with a stirrer, a reflux condenser, a thermometer and a dropping funnel, 56.6 g (1.15 mol) of sodium cyanaide and 680 ml (8.77 mol) of N,N-dimethylformamide were charged and 83.8 g (1.10 mol) of carbon disulfide was added thereto dropwise at 20 to 30° C. under stirring. The temperature was being raised to 60° C., and then the mixture was stirred for 3 hours. The reaction solution was cooled to 25° C. and 72.2 g (1.02 mol) of chlorine was introduced into the flask by blowing, and then the temperature was raised to 60° C., and the resultant mixture was stirred for 1 hour. The reaction solution was cooled to 5° C. and 400 ml of toluene and 1,000 g of water were added thereto, and then the solution was neutralized with a 10 wt.%-aqueous sodium carbonate solution. The precipitated sulfur was removed by filtration and the product was obtained as a dark black toluene solution containing a large amount of tar component by liquid separation.

This toluene solution was analyzed by a HPLC absolute calibration curve method. As a result, it was found that the content of 3,4-dichloro-5-cyanoisothiazole was 11.4% by weight and the yield was 53% with respect to the theoretical yield. The by-produced sulfur was obtained in a wt. amount which was 2.4 times that of the intended product.

Comparative Example 2

Process Using No Aprotic Polar Solvent

In a 50 ml four-necked flask equipped with a stirrer, a reflux condenser and a thermometer, 22.0 g (0.27 mol) of succinonitrile was charged, the resultant mixture was stirred by using a magnetic stirrer while the temperature was being raised to 120° C. While sufficiently paying attention, 65.0 g (0.92 mol) of chlorine was introduced into the flask by blowing for 11 hour. The temperature was cooled to room temperature, and then the resultant reaction solution was transferred to a 1 L four-necked flask equipped with a stirrer, a reflux condenser, a thermometer and a dropping funnel. Under stirring, 87.8 ml (1.1 mol) of sulfur monochloride was added thereto at 20 to 25° C.

Then, the temperature was heated to 100° C. and the mixture was stirred for 6 hours. However, 3,4-dichloro-5-cyanoisothiazole could not be obtained.

(GC Analysis Method)

With respect to the details of the above-mentioned GC analysis method, the following documents can be referred to, as desired:

(a): "Shin-Jikkenkagaku Koza (A New Course in Experimental Chemistry) No. 9, edited by The Chemical Society of Japan, Bunseki Kagaku (Analytical Chemistry) II", pp. 60 to 86 (1977), published by Shingo Iizumi, MARUZEN Co., Ltd. (for example, it is possible to refer to page 66 of this document, with respect to liquids for a stationary phase to be usable for a column); and (b): "Jikkenkagaku Koza (Course in Experimental Chemistry) No. 20-1; edited by The Chemical Society of Japan, Bunseki Kagaku (Analytical Chemistry)", 5th edition, pp.121 to 129 (2007), published by Seishiro Murata, MARUZEN Co., Ltd. (for example, it is possible to refer to pages 124 to 125, with respect to methods of specifically using of a hollow capillary separation column).

(HPLC Analysis Method)

With respect to the details of the above--mentioned HPLC analysis method, the following documents can be referred to, as desired:

(c): "Shin-Jikkenkagaku Koza (A New Course in Experimental Chemistry) No. 9, edited by The Chemical Society of Japan, Bunseki Kagaku (Analytical Chemistry) II", pp. 86-112 (1977), published by Shingo Iizumi, MARUZEN Co., Ltd. (for example, it is possible to refer to pages 93 to 96 with respect to a combination of a filler and a mobile phase to be usable for a column); and (d): "Jikkenkagaku Koza (Course in Experimental Chemistry) No. 20-1, edited by The Chemical Society of Japan, Bunseki Kagaku (Analytical Chemistry)", 5th edition, pp. 130 to 151 (2007), published by Seishiro Murata, MARUZEN Co., Ltd. (for example, it is possible to refer to pages 135 to 137 with respect to specific methods and conditions for reversed-phase chromatographic analysis)

INDUSTRIAL APPLICABILITY

The present invention provides a novel industrial process for producing 3,4-dichloro-5-cyanoisothiazole. According to the present invention, it is possible to use a nitrile compound represented by the general formula (1) as a raw material and to produce a high-purity 3,4-dichloro-5-cyanoisothiazole containing no tar component with a high yield in an industrial scale, without using a raw material having a high toxicity, an expensive catalyst or a transition metal, or a specially designed reactor, by a simple operation under a mild condition, while suppressing by-production of waste. Further, since a harmful waste derived from a catalyst or a transition metal is not emitted in this process, it is easy to treat the resultant waste, and accordingly the environmentally friendly industrial utility value thereof is high.

The invention claimed is:

1. A process for producing 3,4-dichloro-5-cyanoisothiazole represented by formula (3):

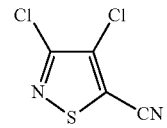

(3)

the process comprising:

reacting a nitrile compound represented by formula (1):

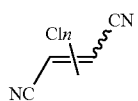

(1)

(wherein "n" denotes an integer of 0 to 2), or a mixture thereof, with sulfur chloride represented by formula (2):

$S_mCl_2$ (2)

(wherein "m" represents an integer of 1 to 2), or a mixture thereof, in an aprotic polar solvent.

2. A process for producing 3,4-dichloro-5-cyanoisothiazole according to claim 1, wherein the nitrile compound is a nitrile compound of formula (1) wherein "n" is 0.

3. A process for producing 3,4-dichloro-5-cyanoisothiazole according to claim 1, wherein the nitrile compound is a nitrile compound represented by formula (1) wherein "n" is 1.

4. A process for producing 3,4-dichloro-5-cyanoisothiazole according to claim 1, wherein the nitrile compound is a nitrile compound represented by formula (1) wherein "n" is 2.

5. A process for producing 3,4-dichloro-5-cyanoisothiazole according to claim 1, wherein the nitrile compound is a mixture of nitrile compounds, wherein each nitrile compound is represented by formula (1) wherein "n" is 0, 1 or 2.

6. A process for producing 3,4-dichloro-5-cyanoisothiazole according to claim 1, wherein the aprotic polar solvent is an amide-based aprotic polar solvent or a carbonate ester-based aprotic polar solvent or a mixture thereof.

7. A process for producing 3,4-dichloro-5-cyanoisothiazole according to claim 6, wherein the aprotic polar solvent is dimethylformamide, dimethylacetamide, diethylacetamide, N-methylpyrrolidone, tetramethylurea, hexamethylphosphoric triamide, ethylene carbonate or propylene carbonate, or a mixture thereof.

8. A process for producing 3,4-dichloro-5-cyanoisothiazole according to claim 6, wherein the aprotic polar solvent is dimethylformamide, dimethylacetamide, diethylacetamide, N-methylpyrrolidone, tetramethylurea or a mixture thereof.

9. A process for producing 3,4-dichloro-5-cyanoisothiazole according to claim 1, wherein the sulfur chloride represented by formula (2) wherein "m" is 1 or 2, or a mixture thereof is prepared in a reaction system.

10. A process for producing 3,4-dichloro-5-cyanoisothiazole according to claim 1, wherein sulfur chloride represented by formula (2) is sulfur monochloride, wherein "m" is 2.

11. A process for producing 3,4-dichloro-5-cyanoisothiazole according to claim 1, wherein the nitrile compound represented by formula (1):
(1)
(wherein "n" is 1 or 2), is produced by chlorination of succinonitrile represented by formula (4):
(4)
\* \* \* \* \*